United States Patent [19]

Faure

[11] Patent Number: 5,192,272
[45] Date of Patent: Mar. 9, 1993

[54] PACK FOR ADMINISTRATION OF STERILE LIQUIDS INCLUDING PHARMACEUTICAL, NUTRIENT AND ENERGY-SOURCE LIQUIDS

[76] Inventor: Jean-Marie Faure, 100, avenue du Président Kennedy, 75016 Paris, France

[21] Appl. No.: 603,323

[22] Filed: Oct. 25, 1990

[30] Foreign Application Priority Data

Oct. 26, 1989 [FR] France ................................ 89 14037

[51] Int. Cl.$^5$ ............................................. A61M 5/00
[52] U.S. Cl. ........................... 604/141; 128/DIG. 12; 604/132
[58] Field of Search ................. 604/150, 141, 132, 32, 604/133, 134, 135, 136, 153; 128/DIG. 12

[56] References Cited

U.S. PATENT DOCUMENTS

| | | | |
|---|---|---|---|
| 3,507,278 | 4/1970 | Werding | 604/141 |
| 3,640,277 | 2/1972 | Adelberg | 604/141 |
| 3,832,067 | 8/1974 | Kopf et al. | |
| 3,838,794 | 10/1974 | Cogley et al. | 604/141 |
| 4,193,398 | 3/1980 | Refson | |
| 4,457,752 | 7/1984 | Vadasz | 604/153 |
| 4,513,796 | 4/1985 | Miller et al. | 604/153 |
| 4,613,327 | 9/1986 | Tegrarian | 604/141 |
| 4,626,243 | 12/1986 | Singh et al. | 604/141 |
| 4,640,445 | 2/1987 | Yamada | |
| 4,684,367 | 8/1987 | Schaffer et al. | 604/141 |
| 4,913,702 | 4/1990 | Yum et al. | |
| 4,955,860 | 9/1990 | Ruano | 128/DIG. 12 |

FOREIGN PATENT DOCUMENTS

| | | |
|---|---|---|
| 0077189 | 4/1983 | European Pat. Off. |
| 0295504 | 12/1988 | European Pat. Off. |
| 3446909 | 10/1985 | Fed. Rep. of Germany |
| 3507818 | 7/1986 | Fed. Rep. of Germany |
| 2346238 | 10/1977 | France |
| 8900868 | 2/1989 | PCT Int'l Appl. |
| 2197691 | 5/1988 | United Kingdom |

*Primary Examiner*—Paul J. Hirsch
*Attorney, Agent, or Firm*—Perry Carvellas

[57] ABSTRACT

A pack for slow administration to a patient of extremely accurate volumes of sterile, for example pharmaceutical, nutrient or energy-source liquid, comprises in combination at least three systems adapted to be interconnected. The first system is a flowrate regulator. The second system is, for each sterile liquid administered, a sterile bag with a mobile, flexible and continuous wall which delimits an internal cavity in which is at least one opening enabling it to communicate selectively with the exterior. The third system is a solid or fluid piston operating on the interior or exterior side of the wall of said bag to vary its volume, and, in the case of a fluid piston, at least one alarm means indicating any leak in the wall or one of the walls of the bag, adapted by its existence or its properties to convert non-perceptible leakage into a perceptible phenomenon.

37 Claims, 3 Drawing Sheets

PACK FOR ADMINISTRATION OF STERILE LIQUIDS INCLUDING PHARMACEUTICAL, NUTRIENT AND ENERGY-SOURCE LIQUIDS

BACKGROUND OF THE INVENTION

1. Field of the invention

The present invention concerns packs for administration of sterile liquids including pharmaceutical, nutrient and energy-source liquids.

2. Description of the prior art

Each patient requires a different and extremely accurate dose of a different active product administered over an accurate time period in accordance with a personalized medical prescription that must be complied with absolutely.

In the current state-of-the-art this always requires as a preliminary stage the sterile transfer of a very accurate volume of sterile liquid from its industrial packaging to a delivery system which must be capable of administering aseptically and with extreme accuracy specified volumes of the sterile liquid.

This is particularly true in respect of cytostatic agents which are highly toxic and very aggressive. These products are therefore transferred in specialist hospital units employing special sterile rooms, sterile bubbles and laminar flow extractor cabinets in which the operative wearing breathing apparatus and gloves for protection measures out the required volume with extreme accuracy, transfers it into a special sterile transfer package and then places the latter in a sterile heat-sealed sachet which is then sent to the room of the patient concerned where the nurse, after opening the sachet, carries out a second transfer into the large capacity container of what is known as an injectable mass solute, the delivery system used most frequently in hospitals. These manual operations entail two transfers and require an additional and special transfer package, which makes them very costly, very difficult and very dangerous, not only to the preparation operative and to the nurses, because of the aggressive nature of these products, but also to the patients because the risks of contamination by microbes are increased by the number of transfers. Also, this first type of delivery system has many other disadvantages: very imprecise administration requiring constant and subjective surveillance by a nurse, with the attendant economic consequences, the impossibility of moving patients without a third person accompanying them and holding the large capacity container above them at all times, and the impossibility of administering such treatment at home.

In a second type of delivery system a motor moves the piston of a disposable syringe. This simplifies the transfer problem but because it requires a powerful motor and because the piston sticks easily, the delivery system is heavy, costly and sophisticated and incorporates safety systems (because of the risk of the motor racing), battery or AC line voltage power supply, all of which makes the treatment of ambulatory patients difficult and time-consuming.

A third type of delivery system is the infuser. Although this solves the weight problem it has many other disadvantages.

Filling requires an additional sterile transfer package in the form of a sterile syringe. When this has been filled, it must be used immediately because the dispensing of the sterile liquid begins. This rules out its advance preparation in specialist hospital units and industrial prepackaging, the latter being even less feasible given that the infuser is too costly because the entire system, comprising a pack with strongly elastic walls and an accurate flowrate regulator, is disposable. Because the system is not re-usable and because the liquid to be administered flows through it, apart from the economic repercussions, the volumes dispensed are not the same for liquids which have different viscosities, they cannot be varied for different patients to suit the medical prescription, and it is impossible to administer suspensions as these would clog the regulator. In some cases the elastomer constituting the walls of the pack, which is always the same, interacts with the product to be administered, in other words the product and the container may be incompatible.

Faced with the disadvantages summarized above, a general objective of the invention is to provide a pack for administering sterile liquids suitable for industrial prepackaging or for filling by aspiration direct from any other form of industrial packaging and then dispensing with extreme accuracy specified volumes of sterile liquids, and in particular dispensing these liquids with an extremely accurate preset flowrate determined by the medical prescription, which pack is capable of solving the problem of previous transfer into a delivery system, is capable of administering different volumes for different patients, offers a completely free choice of component materials to suit the product to be administered so that there is no interaction between them, is sufficiently light in weight and sufficiently reliable to be usable for treating ambulatory patients in total safety and with no requirement for any supply of electrical power, and enables a significant reduction in the weight and the cost of the apparatus with re-usable component parts.

SUMMARY OF THE INVENTION

The present invention consists in a pack for slow administration to a patient of extremely accurate volumes of sterile, for example pharmaceutical, nutrient or energy-source liquid, comprising in combination at least three systems adapted to be interconnected, namely:
- a flowrate regulator,
- for each sterile liquid administered, a sterile bag with a mobile, flexible and continuous wall which delimits an internal cavity in which is at least one opening enabling it to communicate selectively with the exterior and,
- a solid or fluid piston operating on the interior or exterior side of the wall of said bag to vary its volume, and, in the case of a fluid piston, at least one alarm means indicating any leak in the wall or one of the walls of the bag, adapted by its existence or its properties to convert non-perceptible leakage into a perceptible phenomenon.

Other advantages and characteristics of the invention will emerge from the following description of some embodiments of the invention given with reference to the appended drawings.

DETAILED DESCRIPTION OF THE PREFERRED EMBODIMENTS

Figures 1, 4:
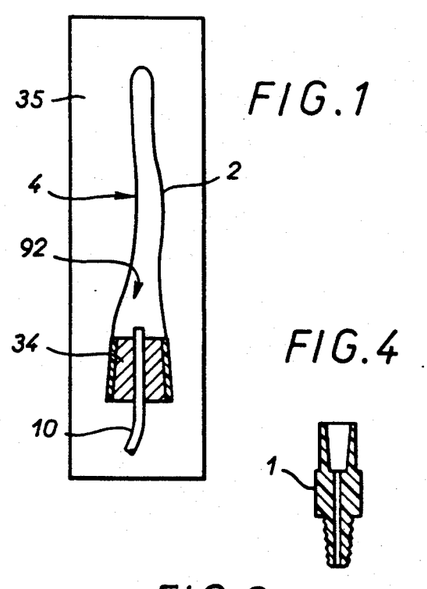
FIG. 1 is a schematic view in elevation of one of the systems of the combination in accordance with the invention.
FIG. 4 is a schematic view in elevation of a flowrate regulator.

Referring to FIG. 1, a bag 2 has a continuous, flexible and mobile wall attached to an elastic material plug 34 and communicating with the exterior through an opening (tube 10) constituting the point of departure of the system for administration of a product to a patient (not shown). This system constitutes one element of the pack in accordance with the invention and may be supplied in a sterile heat-sealed sachet 35. The wall of the bag 2 may be of single-layer or multiple-layer construction, in the latter case with the layers attached together or independent of each other. A structure of this kind has advantages which will emerge as the following description proceeds.

Figures 2, 3:
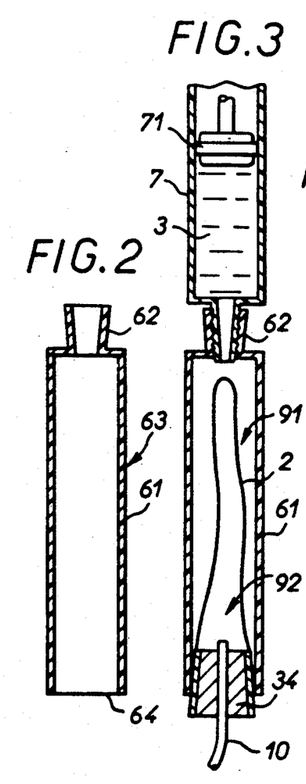
FIG. 2 is a schematic view in elevation of one embodiment of an intermediate member serving as a connection member between the systems of the combination in accordance with the invention.
FIG. 3 is a schematic view in elevation of one form of pack in accordance with the invention.

FIG. 2 shows a part 61 used as a connector in the assembly shown in FIG. 3. It is generally cylindrical and has respective orifices 62 and 64 at opposite ends. It is adapted to be connected at the end with the orifice 64 to the bag 2 (removed from its sachet) and at the end with the orifice 62 to a syringe 7, for example, as shown in FIG. 3, which syringe has a piston 71 and is completely filled with a liquid 3 referred to hereinafter as the control liquid (with no dead space).

Figure 5:
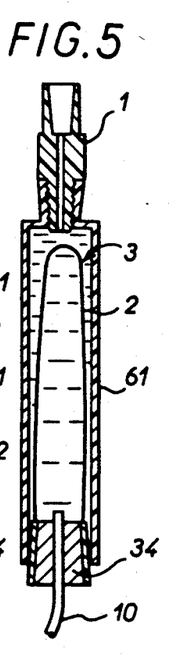
FIGS. 5, 6 and 7 are schematic views in elevation of other combinations of the three systems in accordance with the invention.
Figure 7:
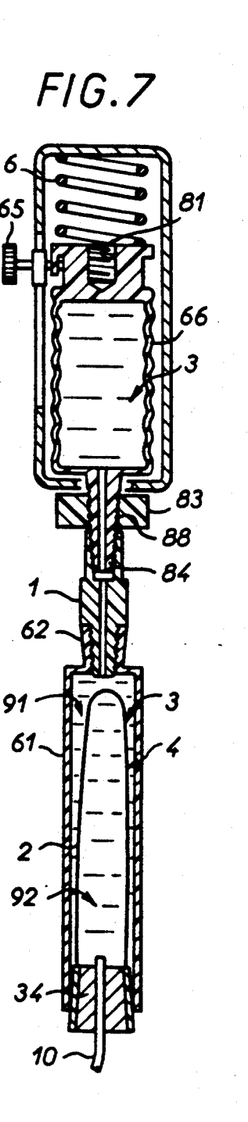

FIG. 4 shows a known type flowrate regulator 1 which can be used in a pack in accordance with the invention as shown in FIGS. 5 and 7. A regulator of this kind is connected to the connector 61 filled with control liquid, the bag 2 being filled with the liquid to be administered (see FIG. 5).

Figure 6:
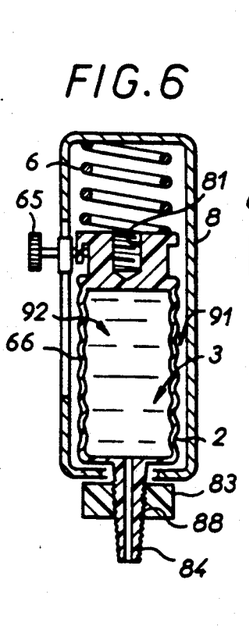

Referring to FIG. 6, the dispenser for any known type control liquid comprises a cylinder 8 enclosing a sealed flexible wall bag 66 at the top of which is a sleeve on which bears a spring 6 accommodated between said sleeve and the upper end of said cylinder 8. The position of the sleeve can be adjusted heightwise by a locking system 65 operable from the exterior and the compression of the spring 6 can be adjusted by altering the position of the sleeve using a piston arm (not shown) that can be screwed into and out of the screwthread 81 through an orifice at the upper end of the cylinder 8.

FIG. 7 shows how this control liquid dispenser can be connected to the regulator 1 and to the connector 61 enclosing the bag 2 and its accessories.

A pack of this kind is used in the following manner:

The sachet 35 is torn open and the bag 2 removed from it with its plug 34 and its tube 10. The bag and the connector 61 are then assembled to the syringe 7 filled with control liquid 3. Note that the connector 61 and the syringe 7 do not need to be sterile. The interior cavity 91 is filled with said control liquid, air is drawn into the syringe 7 to eliminate the least dead space in the cavity 91 and the cavity 91 is filled again with the control liquid.

With the end of the administration system (not shown in the figure) extending into the liquid to be administered contained in industrial packaging, by moving the piston 71 of the syringe 7 the precise, total and specific volume of liquid to be administered is drawn into the bag 2.

By moving the piston 71 in the opposite direction all traces of air are expelled from the bag 2 and from the administration system so that there remains no dead space, as in the chamber 91. The connector 61 is disconnected from the syringe and connected to the flowrate regulator 1 in turn connected to the control liquid dispenser 8.

When administration of the sterile liquid is to begin the administration system is fitted to the patient (injection needle in a vein, for example) and the locking-unlocking member 65 is released. Administration begins.

The control liquid from the dispenser 8 passes through the flowrate regulator 1 which determines accurately the volume V entering the chamber 91 during a specific time period. As the liquids are incompressible and as there is no dead space, a strictly identical volume V of liquid to be administered leaves the bag 2 during this same time period and is administered to the patient.

The stated objectives are achieved:

- Extreme accuracy: incompressibility of the liquids. No dead space→V=V.

- As the liquid flowing through the flowrate regulator is always the same (the control liquid) the volume dispensed is always the same, irrespective of the viscosity of the liquid to be dispensed.

- The only sterile member is the bag 2.

- The bag 2 is therefore the only part that is not reusable, i.e. the only consumable element, which is highly beneficial from the economic point of view.

- The flowrate regulator does not need to be sterile and is therefore easily and quickly interchangeable. This means that the regulator to be used can be chosen quickly according to the volume required for a particular patient and the medical prescription.

- As the liquid administered does not pass through the flowrate regulator, suspensions, emulsions and solutions can be administered.

The transfer from the industrial packaging to the delivery system is achieved in a very simple way without any special additional sterile transfer packaging:

- either as described previously;

- or by prepackaging the product to be administered directly in the bag 2, either in liquid form or in solid form. In the latter case it remains only to add the liquid to convey or dissolve this product.

The device described above does not require a motor and therefore does not require any source of electrical or mechanical energy, eliminating the risk of power failure and of the motor racing.

The flowrate regulator 1 may be connected to any system for dispensing a control liquid, for example, in a hospital environment, a water supply pipe with or without a pressure indicator and filter.

The flowrate regulator may be any accurate liquid dispensing system operating by displacement of a piston, peristaltic action, etc; it may even be a prior art infuser and in this case the infuser will be re-usable.

The apparatus in accordance with the invention includes alarm means (to be described later) to achieve total safety.

Figure 8:
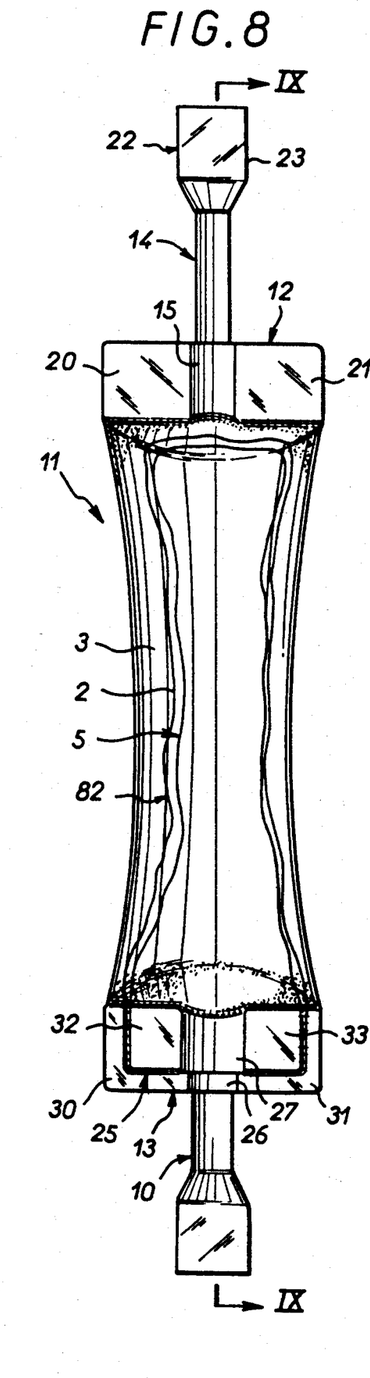
FIG. 8 is a view in elevation of an advantageous embodiment of one part of a pack in accordance with the invention.
Figure 9:
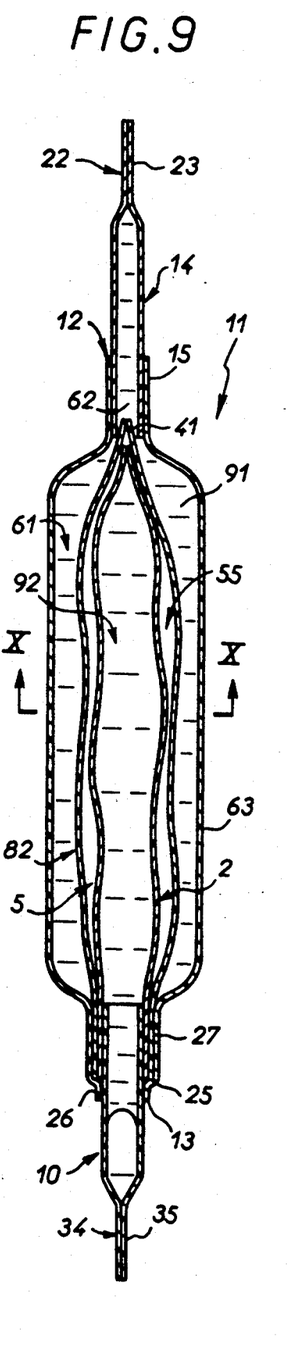
FIG. 9 is a view in cross-section on the line IX—IX in FIG. 8.
Figure 10:
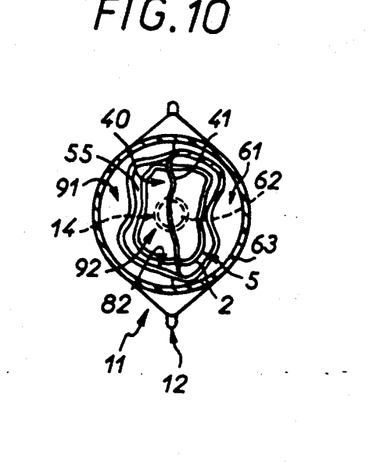
FIG. 10 is a view in cross-section on the line X—X in FIG. 9.

In a second embodiment shown in FIGS. 8 through 10 the pack in accordance with the present invention comprises a chamber 61 with a continuous wall in which is an orifice 62 for communication with the exterior. The wall 63 of the chamber 61 defines a constant volume interior cavity 91 and encloses a sealed bag with continuous, flexible and mobile double walls 5 and 82. The wall 5 in turn delimits an internal cavity 92 of variable volume $V_x$ said internal cavity 92 communicating with the exterior through a tube 10 open to the exterior of the chamber 61.

The chamber 61 is in the form of a flexible and transparent tube 11 of thermoplastic material heat-welded in areas 12 and 13 at its ends.

The first end portion 12 of the tube 11 is formed by heat-welding the interior surface of the wall 63 around a tube section 14 which is sealed to the orifice 62.

The end portion 12 therefore comprises a generally cylindrical central area 15 in which the tube 11 is welded to part of the tube section 14. The central area 15 is extended on each side by a generally flat flange 20 and 21.

At the end of the tube 14 opposite that connected to the orifice 62 is a removable hermetic seal 22 obtained by crushing the tube 14 and heat-welding it to itself to form a weld 23. It is removable in the sense that the tube 14 can easily be cut below the weld 23.

Of course, any removable means of hermetically sealing a flexible tube could be used, including plugs or clamps. The tube 14 like the tube 10 can be entirely or partly made from an elastomer material which can be easily pierced in a sealed manner by a single-chamfer or double-chamfer needle.

The other end portion 13 of the tube 11 is formed by heat-welding the tube 11 to a first end area 25 of the bag 2 which, before welding, is in the form of a double-wall cylindrical sleeve with thin walls 5 and 82 or, for example, three stacked films heat-welded along their entire length.

The end portions 13 and 25 obtained by welding together the facing surfaces of the tube 11 and the bag 2 enclose a tube section 10 which therefore passes at a precise location through the wall of the chamber 61 without breaking the seal of this chamber at this location.

The end portions 13 and 25 therefore have respective central areas 26 and 27 resulting from the welding of the tube 11 to the bag 2 which is in turn welded around part of the tube section 10.

The generally cylindrical central areas 26 and 27 are continued on each side by flat flanges 30, 31, 32, 33 respectively of the tube 11 and of the sleeve of the bag 4.

The tube 11, the tube 14 and the tube section 10 are substantially coaxial.

The tube section 10 comprises, at the end outside the tube 11, a removable hermetic seal 34 having the same characteristics as the seal 22 described above, formed by a weld 35.

In this embodiment the bag 2 has a second end portion 40 heat-welded to both walls 5 and 82 simultaneously to form a weld 41.

This weld provides a seal isolating the internal cavity 92 from the bag 2 and creates a third sealed cavity 35 between the two walls 5 and 82.

This embodiment operates in the same way as already described for the first embodiment, but in this case the connections are made directly by the tube 14 to the syringe 7 (see FIG. 3) and then to the flowrate regulator 1. If, as shown in FIG. 9, the pack is supplied with the cavities 91 and 92 respectively filled with the control liquid and the sterile liquid to be administered, the syringe 7 is not required and the flowrate regulator 1 is connected directly to the tube 14 using any known connection means.

The two sterile cavities 91 and 92 may be interchanged in the sense that the control liquid may be in the cavity 92 and the sterile liquid to be administered in the cavity 91. This introduces an additional advantage, namely the possibility of choosing a material different than that constituting the bag, which has to be flexible or elastic, which may introduce problems of incompatibility between the material of the bag and the product contained in the bag. It is therefore possible to select for the chamber 61 any appropriate material such as (to give some non-limiting examples): glass, metal, ceramic, plastics material, and the chamber may be formed by any known process suitable for the material employed, such as (to give some non-limiting examples) blowing, vacuum-forming, molding, machining. In this embodiment the bag 2 has a double wall. It could have a single wall or a multiple wall.

Not only may the functions of the two cavities 91 and 92 be interchanged, but all possible variants are within the scope of the invention, the pack in accordance with the invention consisting of the sealed assembly (FIGS. 1 through 9) of two preconnected or connectable members comprising a chamber 61 and deformable bag 2 contained in said chamber, not communicating with each other but each communicating individually and separately with the exterior through at least one respective opening 62 and 10, so that any variation in the volume of one causes an equal variation in the volume of the other.

In the embodiment shown in FIGS. 8 through 10 the chamber and the bag each communicates with the exterior through one orifice only, respectively the tube 14 and the tube 10. This example is not limiting on the invention and there may be any number of orifices.

In this embodiment the two orifices are closed, the bag 2 and the chamber 61 each containing a respective liquid. If the bag 2 and the chamber 61 are supplied empty the pack may be supplied with a single closure, closure of the volume which must be sterile, volume to be used for administrating the sterile liquid. The same applies if the pack is supplied containing in the bag 2 or in the chamber 61 a single liquid namely the liquid to be administered or a medication or a nutrient or an energy-source product in solid form.

The volume and the dosing with medication or other substance of the liquid filling the cavity 91 or 92 are precisely determined and may be written on the tube 1 in any way. If the bag 2 and the chamber 61 are supplied empty it is also possible not to make any closure, the pack being supplied in a sterile heat-sealed sachet that can be peeled open.

All these solutions, combined to a greater or lesser degree, are possible. If the tube 11 is of reasonable diameter, the weld 12 may be eliminated, the tube 14 may be eliminated and the source of control fluid may be connected directly to the tube 11.

In this embodiment the bag 2 and the chamber 61 are simultaneously heat-welded around and to the tube 10.

To give a non-limiting example, it is possible to weld first the wall 5, then the wall 82 of the bag 2, then the wall 62 of the chamber 61, either one on top of the other or at successive and different positions along the tube 10.

The bag 2 and the tube 10 may be in one piece in which case only one heat-weld is required, between the chamber 61 and the appropriate part of the bag 2.

In this embodiment the heat-welds are executed on cylindrical tubes. The pack in accordance with the invention may be fabricated by any known process including molding, blowing, adhesive bonding and others. The bag may also be fabricated by processes used for condoms, plastics or rubber gloves, large capacity bags for solutes.

Figure 11:
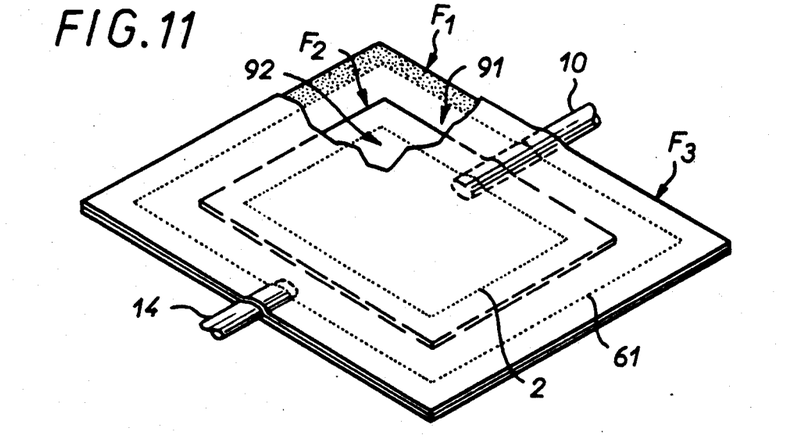
FIG. 11 is a schematic view of one embodiment of a pack according to FIG. 8.

To give a further example using heat-welding, it would be possible to start with films instead of tubes. This possibility is shown by FIG. 11. Starting with two films $F_1$ and $F_2$ of different size, in a first stage the smaller film is welded to the larger all around its perimeter and onto and around the tube 10. This produces the bag 2-cavity 92. In a second stage a third film $F_3$ the same size as the larger film is heat-welded all around its perimeter and onto the tube 14, as well as onto and around the tube 10, producing the chamber 61-cavity 91.

If the bag 2 is required to have a double wall, instead of the smaller film previously employed either two smaller films the same size already heat-welded together are used or two such films are heat-welded simultaneously or one after the other around and onto the tube 10 and onto the larger film.

When administration is finished, it is possible to refill the pack with the liquid previously administered or with a different sterile liquid, for example a liquid containing a different concentration of the same medication or a different medication. To carry out this operation the tube 10 is closed externally by means of a clamp. The tube 10 is in this case made from a relatively thick elastomer material; it is pierced by a hollow needle connected to a reservoir containing the second liquid, so that the needle enters the interior of the tube 10 which is in fluid communication with the cavity 92. The cavity 92 is then filled either by exerting slight pressure on the sterile liquid with concomitant evacuation of the control liquid from the cavity 91 or by aspirating the control liquid causing the sterile liquid to be aspirated into the cavity 92. As the tube 10 is closed off, no liquid is administered to the patient during filling. Any other temporary connection means may be employed instead of piercing the tube 10, for example three-way valves, piercable plugs, Luer Tees.

When the filling of the cavity 92 is finished the connection to said reservoir containing the second liquid is removed or closed off and administration resumes under the action of the control fluid.

The pack in accordance with the invention enables the dispensing of a specific volume of a sterile liquid in particular a medication solution or suspension to be injected slowly. There will now be described means of reversibly hermetically sealing one of said cavities 91, 92, containing a first liquid or solid substance intended to be mixed with a second liquid or solid substance to obtain a reaction producing in the chosen volume and at a substantially constant flowrate a gas to serve as a control fluid.

Any known reaction between two substances producing a gas may be employed.

This reaction may use a regular or irregular slow release tablet releasing regularly or at a specified point a product reacting with a liquid or another product dissolved in a liquid to release a gas at a specific flowrate. This may be, for example, a tablet containing, with appropriate binders and excipients, a peroxidase releasing oxygen contained in oxygenated water ($H_2O_2$ solution). Instead of being enzymatic the reaction may be chemical. The tablet may be a tablet of sodium bicarbonate reacting with a weakly acid solution to release carbon dioxide.

In this embodiment the fluid piston is a gas piston. As gases are compressible, if the flowrate regulator is connected to the cavity containing the control fluid, as in the previous examples (in which steps were taken to eliminate all traces of gas, i.e. of dead space, exactly because of this compressibility) the accuracy will be low. The flowrate regulator is therefore connected to the cavity containing the sterile liquid to be administered, and the same applies if the control fluid is not fabricated in the packaging but fed in by a pump. This solution may also be adopted in the examples previously described, in other words the flowrate regulation may be applied to the circuit for the liquid to be administered.

Whichever cavity it is connected to, the flowrate regulator may be a calibrated capillary tube of specific diameter, length and angle or a micro-orifice of calibrated diameter. This micro-orifice may be in the wall of the chamber and/or the bag; it then constitutes the opening to the exterior or one of these openings. Whatever material is used, the micro-orifice is advantageously formed with very high accuracy using a laser.

Figure 12:
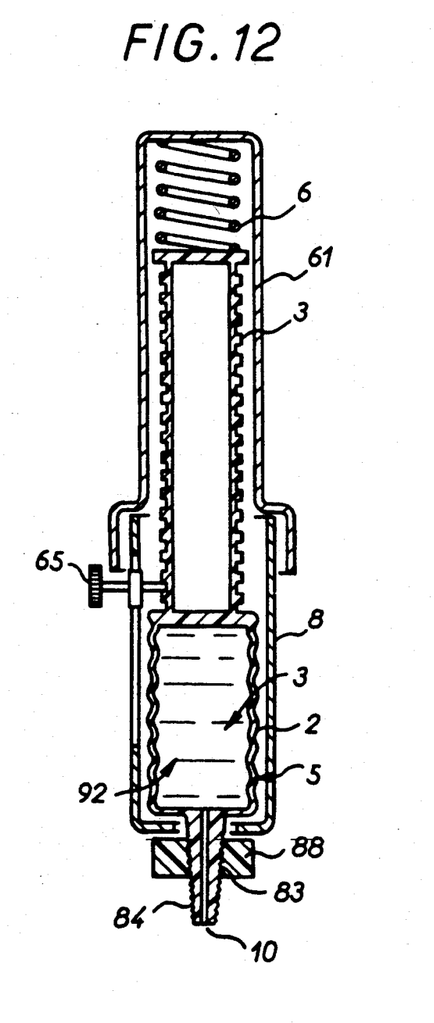
FIG. 12 is a view in elevation and cross-section of another embodiment of a pack in accordance with the invention.

In a third embodiment shown in FIG. 12 the pack uses a solid piston instead of a fluid piston to operate on the wall of the bag 2 and so vary its interior volume. The bag 2 with plastics material, elastomer or other material continuous, flexible and mobile walls is supplied sterile in a sterile heat-sealed sachet, as in FIG. 1, and either empty or containing a medication, nutrient or energy-source product. The bag may be attached by adhesive bonding, heat-welding, screwing or any other means to a piston 3 whose exterior wall is notched, or it may be independent of the piston, in which case the connection is made by the user (by screwing or otherwise). With the locking-unlocking system 65 released, the system is inserted into the part 8 where it is fixed by screwing, by clamping or the like the parts 83 through 88.

If the bag 2 is empty or contains a solid product the first stage is to feed a sterile liquid into the bag 2, as follows:

The opening to the exterior in the bag 2 is a male Luer cone (it could equally well be, for example, a self-sealing elastomer or latex plug, adapted to be pierced by a double-chamfered needle, or the entire bag could be made from an elastomer material). A sterile needle is fitted to it and dipped into the sterile liquid in its industrial packaging. By pulling out the piston 3 all of the required and prescribed volume is drawn up with great accuracy.

With the needle pointing upwards, the piston is pressed in to expel any air in the bag. The locking-unlocking system 65 is locked and the part 61 is screwed to the part 8. The flowrate regulator 1 is substituted for the needle and connected to the administration system.

When the system is fitted to the patient (needle in a vein, for example), the locking-unlocking system 65 is released. The administration begins.

As in the first embodiment, the spring 6 may be replaced by any known means, for example: compressed air, a system for releasing a gas as previously described, or any mechanical, hydraulic or pneumatic system for moving the piston 3 (for example, in hospital use, direct connection to a mains water supply with or without a pressure gauge).

In this embodiment also the bag may be a single-wall or double-wall or multiple-wall bag. Alarm means may be provided, but is not needed in this embodiment because leaks in the bag do not represent any hazard to the patient.

On the other hand, if the piston is a fluid piston and a leak occurs in the wall of the bag, this represents a hazard to the patient as some of the control fluid may be administered to the patient without this being noticed.

To eliminate this hazard the pack in accordance with the invention uses alarm means.

The alarm means converts the non-perceptible leakage phenomenon into a perceptible phenomenon: it may be placed at any location on the pack, and in particular (to give some non-limiting examples) in any of the cavities 91 or 92 or 55 (if the latter exists, that is to say if the bag has at least two walls).

The alarm means may be a solid, liquid or gas, soluble in the control liquid and/or in the liquid to be administered, insoluble in the control liquid and/or the liquid to be administered, made up of one or more elements.

The phenomenon used may be perceptible and perceived at any location on the pack and/or external to the pack, either by the senses (to give some non-limiting examples: visually by the disappearance and/or the change of one or more colors and/or the modification of the transparency or limpidity or any other detectable physical parameter), or automatically using devices of greater or lesser sophistication, for example devices generating any kind of perceptible signal.

The various products or systems that can be used as alarm means and the automatic equipment capable of reading a signal are so numerous that they will not all be described here. The description will necessarily be limited to a few explanatory and non-limiting examples given below with reference to FIG. 9.

I. The bag 2 is a single-wall bag.

I.1. A coloring agent is dissolved in the control liquid in the cavity 91 (for example, methylene blue, Paris blue, gentian violet, congo red, gonacrene, trypan blue, phenolsulfonephthalein).

If a leak occurs in the wall of the bag 2 coloration appears in the bag 2 and is detectable either visually or by a light-sensitive device.

I.2. Sodium chloride is dissolved in the liquid to be administered, which also renders it isotonic. The control liquid is extremely pure distilled water contained in the cavity 91 into which dips a metal probe (or the metal flowrate regulator used as a conductive probe) connected to equipment sensitive to an electrical constant, which in this example is the conductivity. If there is a leak in the wall of the bag 2, chlorine and sodium ions enter the cavity 9 and the conductivity increases suddenly. Detection could instead be performed by electrodes specific to detecting chlorine or sodium.

I.3. It is also possible to combine the above two approaches, i.e. to duplicate the alarm means.

Sodium chloride in the cavity 92 and dissolved coloring agent in the cavity 91, so that there would be an automatic alarm and a visual alarm confirming the latter.

II. The bag 2 is a double-wall (or multiple-wall) bag.

II.1. The three systems described are also usable here, the cavity 55 then having the function that the cavity 92 or the cavity 91 previously had.

II.2. The detector is a vacuum that is deliberately created in the cavity 55 during fabrication of the pack. If there is a leak in the wall 5 or 82 this space immediately fills with one of the liquids and the user is alerted immediately.

II.3. The detector is a coloring agent placed in the cavity 55. It may be in solution or in solid form, as a marking on one of the walls (one is familiar with what happens when a drop of water or a raindrop falls onto handwriting) or as a fine powder or tablet, fixed to the wall, fixed to another support bonded to the wall or loose in the cavity 55.

If there is a leak in the wall 82: coloration occurs in the cavity 91 and in the cavity 55.

If there is a leak in the wall 5, coloration occurs in the cavity 92 and in the cavity 55.

It is possible to tell which wall is defective and the alarm has a preventive character because as soon as there is a leak in any wall of the cavity 55 there is no longer any communication between the cavities 91 and 92.

The alarm means advises of a hazard which may occur, which may exist, but which has not yet occurred and does not exist yet. If the coloring agent is painted, written or drawn on the wall then this marking will disappear.

II.4. The detector is a product which reacts with the control liquid and with the liquid to be dispensed.

The reaction may be a chemical, enzyme or other reaction.

EXAMPLE

The alarm device is fixed to a cellulose-base support in the cavity 55 or to one of its walls. This product is in the solid state and is insoluble in the control liquid and is insoluble in the liquid to be dispensed. If there is a leak in one wall this product will not pass into the cavity 91 or 92. The product may be, for example, orthotoludineglucoseoxydaseperoxydase from horseradish. Both liquids contain glucose, so if there is a leak from the part 82 or the part 5 the product is colored immediately.

The alarm can be triggered by a color change: if the fixed product is cobalt chloride, for example, it is blue when dry. If there is a leak from the part 82 or the part 5 water comes into contact with the product and changes its color to lilac and then to pink.

The alarm can be indicated by the disappearance of a color. If two products which react with each other are placed on the same support, when they are dry nothing happens but if there is a leak from the part 82 or the part 5 water enters the bag 55, wets the support and brings the two products into contact, so that a reaction occurs.

Discoloration will occur, for example, using a calcium salt colored with O-Cresolphthalein and "Complexon" as the second product.

The alarm means may be a gas, for example carbon dioxide. If the fluid piston is a liquid the alarm means may be dissolved in the liquid. If the fluid piston is a gas the alarm means may be mixed with the gas or itself constitute the fluid piston. If lime water is put into the cavity 55, in the event of a leak in the part 82 this liquid becomes cloudy. If a product reacting with $CO_2$, for example a product based on phosphoenol pyruvate is used, coloration will result. Alcohol vapor may also be employed, according to the principle well known to motorists who have undertaken the "breathalyser" test.

The above examples relate to colors, but could equally well use any form of radiation or any electrical modification, and all the examples described may be combined at will.

Note that the alarm means has a specific and significant benefit in that, if a product is prepackaged, it indicates any leak in any wall before the pack is used so that the pack can be discarded because of the risk of poor conservation of the packaged product and the hazard to the patient.

Note also that the twin-wall construction in accordance with the invention considerably increases the shelf life.

Figure 13:
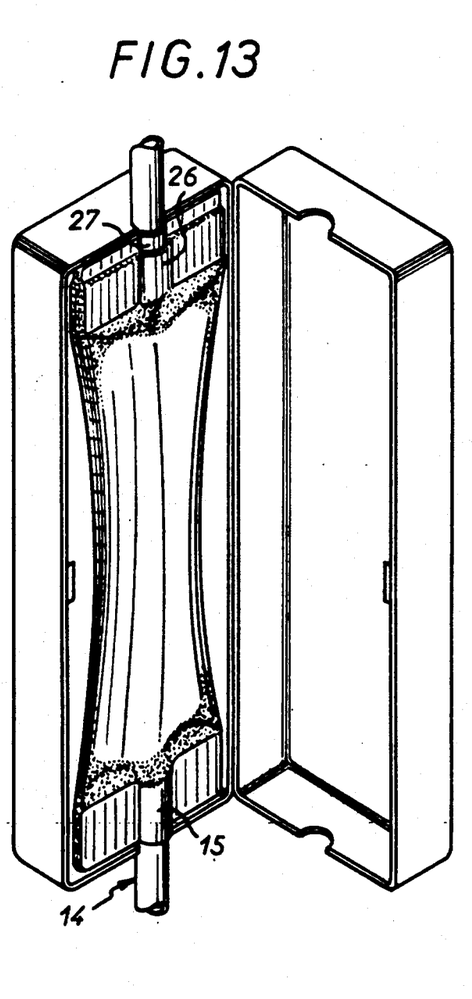
FIG. 13 is a perspective view of a pack from FIG. 8 housed in a transport container with a lid.

An easily transportable pack in accordance with the invention may be provided with a non-deformable protective casing 60 as shown in FIG. 13, for example.

The pack in the embodiment shown in FIGS. 8 and 9 includes a tube 11 that can be accidentally crushed by a force applied to the tube, so reducing its volume. This reduction in volume could lead to a sudden increase in the rate of injection and must be prevented under all circumstances. Placing the pack in the closed casing 60 avoids any possibility of accidental pressure being applied to the tube 11.

Of course, if the chamber 61 has a wall 63 that is sufficiently thick and indeformable the protective casing may be superfluous.

I claim:

1. A container for administering a flowable substance to a patient comprising wall means defining a first chamber adapted to be at least partially filled with the flowable substance, said first chamber having means defining an opening for supplying the flowable substance to the patient, and means for detecting a leak in said wall means comprising means defining a space contiguous with said wall means for receiving the flowable substance accidentally leaked through said wall means, and a leak indicator medium accommodated in the space responsive to the presence of the leaked-in substance to provide a visible indication that a leak has occurred.

2. A container according to claim 1, wherein said medium is a color change medium.

3. A container according to claim 1, wherein said leak indicator is bonded to the means defining a space.

4. A container according to claim 2, wherein the leak indicator medium is disposed loose inside the means defining a space.

5. A container according to claim 3, wherein said wall mean sand said means defining a space together comprise a double wall structure.

6. A container according to claim 2, wherein said medium is a clouding medium.

7. A container according to claim 6, wherein the clouding medium is a gaseous medium adapted to cloud the space in response to contact with the leaked-in substance.

8. The container of claim 1, further comprising a second chamber normally isolated from said first chamber for containing a second flowable substance, a second communication means for communication from the exterior of the container to said second chamber and means for introducing said second flowable substance to said second chamber to effect the flow of said first flowable substance to the patient.

9. A safety container for administering a flowable substance to a patient comprising a first chamber for containing a first flowable substance, first communication means for communication with sad first chamber, a second chamber normally isolated from said first chamber for container a second flowable substance, second communication means for communication means being adapted to supply the corresponding contained flowable substance to the patient, and a third chamber between first and second chambers and normally out of communication with the first and second chambers and defining a reservoir for the second flowable substance accidentally leaked from the second chamber and thereby avoiding contamination of the first flowable substance in the first chamber by the leaked-in second flowable substance from the second chamber, said third chamber containing a leak detector medium for providing a visual indication that the leak has occurred.

10. A container according to claim 9, wherein said leak detector medium is a color change medium.

11. A container according to claim 9, wherein said leak detector medium is bonded to the means defining a space.

12. A container according to claim 9, wherein the leak indicator medium is disposed loose inside the means defining a space.

13. A container according to claim 9, wherein said leak indicator medium is a clouding medium.

14. A container according to claim 13, wherein the clouding medium is a gaseous medium adapted to cloud the space in response to contact with the leaked-in substance.

15. The safety container of claim 9 wherein the first flowable substance is to be administered to the patient and the introduction of the second flowable substance to the second chamber effects the flow of the first flowable substance from the first chamber to the patient.

16. A container for a flowable substance comprising a first chamber having inlet means for supplying a control flowable substance to said first chamber, a second chamber separate from said first chamber for containing a flowable substance to be supplied, and outlet means for connecting said second chamber to a user, said first and second chambers being defined by flexible wall means, a third chamber disposed between wall means separating said first and second chambers, said third chamber defining a reservoir for the flowable substance from either of the first and second chambers in case of a leak in said wall portion, and said third chamber containing means giving a visible indication of said leak to the exterior.

17. A container according to claim 16, wherein said means giving a visible indication of said leak comprises a leak detector medium.

18. A container according to claim 17, said leak detector medium is a color change medium.

19. A container according to claim 17, wherein said leak detector medium is bonded to the means defining a space.

20. A container according to claim 17, wherein the leak indicator medium is disposed loose inside the means defining a space.

21. A container according to claim 17, said leak indicator medium is a clouding medium.

22. A container according to claim 21, wherein the clouding medium is a gaseous medium adapted to cloud the space in response to contact with the leaked-in substance.

23. The container of claim 16 wherein the introduction of a flowable substance to said first chamber effects the flow of the flowable substance from said second chamber to the patient.

24. A pack for administering a flowable substance to a patient comprising a first, inner chamber for containing a first flowable substance, means for communication between said inner chamber and the surroundings, a second, outer chamber substantially entirely surrounding the first chamber for containing a second flowable substance and means for communication between said second chamber and the surroundings, one of said means for communication being adapted to supply the corresponding contained flowable substance tot he patient, said first and second chambers and their respectively flowable substances being normally entirely out of contact and communication with one another, and a third, sealed intermediate chamber disposed between the inner and outer chambers defining a reservoir for accidentally leaked flowable substance from either one of the first and second chambers, said sealed intermediate chamber containing a leak detector medium.

25. A pack according to claim 24, wherein said leak detector medium is a color change medium.

26. A pack according to claim 24, wherein said leak detector medium is bonded to the means defining a space.

27. A pack according to claim 24, wherein the leak indicator medium is disposed loose inside the means defining a space.

28. A pack according to claim 24, wherein said leak indicator medium is a clouding medium.

29. A pack according to claim 28, wherein the clouding medium is a gaseous medium adapted to cloud the space in response to contact with the leaked-in substance.

30. A pack according to claim 24, wherein walls defining said outer chamber and intermediate chamber are transparent.

31. A pack according to claim 24, wherein all said chambers are defined by flexible and transparent walls.

32. A pack according to claim 24, wherein said first, inner chamber comprises a flexible bag.

33. A pack according to claim 24, wherein said third chamber is defined between a pair of bags of similar configuration inside each other, an inner one of said bags defining the barrier between said first and second chambers and the outer one of the bags defining a barrier between the second and third chambers.

34. A pack according to claim 33, wherein said third chamber has opposed sealed ends, access means for the respective first and second chambers extending through one of said sealed ends, open ends of said bags being sealed at one of said opposed ends.

35. A pack according to claim 24, wherein said first, inner chamber is filled with a flowable substance adapted to be administered to an individual and the second chamber is filled with a flowable substance adapted to control the flow of the flowable substance adapted to be administered.

36. A pack according to claim 24, wherein said third chamber comprises a double wall interface between the first and second chambers containing a leak detector medium.

37. The pack of claim 24, wherein the first flowable substance is to be administered to a patient and the introduction of said second flowable substance to said second chamber effects administration of said first flowable substance to said patient.

* * * * *